(12) United States Patent
Bulut et al.

(10) Patent No.: US 11,529,090 B2
(45) Date of Patent: Dec. 20, 2022

(54) SYSTEM AND METHOD FOR DETECTING MOTION SICKNESS

(71) Applicant: KONINKLIJKE PHILIPS N.V., Eindhoven (NL)

(72) Inventors: Murtaza Bulut, Eindhoven (NL); Michel Jozef Agnes Asselman, Helmond (NL); Albertus Cornelis Den Brinker, Eindhoven (NL); Gerrit Maria Kersten, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/768,897

(22) PCT Filed: Nov. 22, 2018

(86) PCT No.: PCT/EP2018/082141
§ 371 (c)(1),
(2) Date: Jun. 2, 2020

(87) PCT Pub. No.: WO2019/110312
PCT Pub. Date: Jun. 13, 2019

(65) Prior Publication Data
US 2020/0337623 A1     Oct. 29, 2020

(30) Foreign Application Priority Data
Dec. 5, 2017   (EP) .................................... 17205374

(51) Int. Cl.
*A61B 5/00* (2006.01)
*A61B 5/024* (2006.01)
*G16H 20/30* (2018.01)

(52) U.S. Cl.
CPC ........ *A61B 5/4023* (2013.01); *A61B 5/02405* (2013.01); *A61B 5/02416* (2013.01); *G16H 20/30* (2018.01); *A61B 2562/0219* (2013.01)

(58) Field of Classification Search
CPC ... A61B 5/01; A61B 5/02405; A61B 5/02416; A61B 5/0816; A61B 5/1032;
(Continued)

(56) References Cited

U.S. PATENT DOCUMENTS

| | | | |
|---|---|---|---|
| 7,949,388 B1 | 5/2011 | Fong | |
| 8,708,884 B1 * | 4/2014 | Smyth | G06F 3/011 706/15 |

(Continued)

FOREIGN PATENT DOCUMENTS

| | | |
|---|---|---|
| DE | 102015011708 A1 | 5/2016 |
| JP | 2006034576 A | 2/2006 |

OTHER PUBLICATIONS

Holmes SR and Griffin MJ. Heart rate and the severity of motion sickness caused by optokinetic stimulation. Journal of Psychophysiology. 2001. 15: 35-42. (Year: 2001).*

(Continued)

*Primary Examiner* — Mallika D Fairchild
*Assistant Examiner* — Shreya Anjaria

(57) ABSTRACT

In order to help reduce the effects of motion sickness, there is provided a method for reducing motion sickness in a subject which comprises acquiring a sequence of video images, extracting measurements of a heart-rate of the subject over a first period of time from the sequence of video images using photoplethysmography (PPG), calculating at least one trend in the measurements, determining a presence of motion sickness when the at least one trend is positive over a first time window, the first time window being included in the first period of time, and generating an event (Continued)

arranged to generate a corrective action. It is often possible to detect the onset of motion sickness before the subject actually feels the symptoms. Indeed, by the time the symptoms appear, corrective action is much less effective. Therefore, by detecting the onset early and alerting the subject so that they can react, it is possible to avoid the attack of motion sickness or, at least, reduce significantly its effects.

20 Claims, 3 Drawing Sheets

(58) Field of Classification Search
CPC ......... A61B 5/1128; A61B 5/113; A61B 5/18; A61B 5/4023; A61B 5/4082; A61B 5/441; A61B 5/6893; A61B 5/7256; A61B 5/7264; A61B 5/7275; A61B 5/746; A61B 2652/0219; A61M 2021/005; A61M 2230/06; A61M 2230/42; A61M 2230/50; A61M 2230/63; G16H 20/30; G16H 30/40; G16H 50/20
See application file for complete search history.

(56) References Cited

U.S. PATENT DOCUMENTS

| | | | |
|---|---|---|---|
| 2014/0135598 A1 | 5/2014 | Weidl et al. | |
| 2014/0176296 A1* | 6/2014 | Morgan | G06F 3/011 340/4.13 |
| 2014/0275832 A1 | 9/2014 | Muehlsteff et al. | |
| 2017/0001005 A1 | 1/2017 | Zhang et al. | |
| 2017/0150930 A1 | 6/2017 | Shikii et al. | |
| 2019/0038180 A1* | 2/2019 | Tzvieli | A61B 5/163 |

OTHER PUBLICATIONS

Stromberg S, et al. Diaphragmatic breathing and its effectiveness for the management of motion sickness. Aerospace Medicine and Human Performance. 86(5). May 2015 (Year: 2015).*

Holmes, S.R. et al. Facial skin pallor increases during motion sickness. Journal of Psychophysiology. 16(3). 150-157. 2002 (Year: 2002).*

Gianaros P.J. et al. Relationship between temporal changes in cardiac parasympathetic activity and motion sickness severity. Psychophysiology. 40(1). 39-44. 2003 (Year: 2003).*

Griffin, M., Newman, M.M. An experimental study of low-frequency motion in cars. Proceedings of the Institution of Mechanical Engineers, Part D: Journal of Automobile Engineering, 218, 1231-1238. 2004 (Year: 2004).*

Cowings,P.S., Suter,S., Toscano,W.B., Kamiya,J., Naifeh.K. "General Autonomic Components of motion sickness", NASA Report, 1986 (Year: 1986).*

Viola et al "Robust Real-Time Object Detection" Proc. of IEEE Workshop on Statistical and Computational Theories of Vision Jul. 13, 2001.

Holmes et al "Correlation between Heart Rate and The Severity of Motion Sickness caused by . . . " Journal of Psychophysiology 15 p. 35-42 (2001).

Gianaros et al "Relationship between Temporal Changes in Cardiac Parasympathetic Activity and Motion Sickness Severity" Psychophysiology 40 (1) p. 39-44 (2003).

International Search Report from PCT/EP2018/082141 dated Mar. 1, 2019.

A. Shupak, C.R. Gordon, "Motion Sickness: Advances in Pathigenesis, Prediction, Prevention, and Treatment", Aviation, Space and Environmental Medicine, vol. 77, No. 12, Dec. 2006.

Holmes, S.R., King, S., Stott, J.R.R., Clemes, S., "Facial skin pallor increases during motion sickness", Journal of Psychophysiology, vol. 16 (3), p. 150-157, 2002.

Berntson G.G., Cacioppo, J.T., Quigley, K.S., "Respiratory sinus arrhythmia: Autonomic origins, physiological mechanisms, and psychophysiological implications", Psychophysiology, 30 (1993), 183-196.

Mert, A., Bles W., Nooij, S.A.E, "Hyperventilation in a Motion Sickness Desensitization Program", Aviation, Space and Environmental Medicine, vol. 78, No. 5, section I, May 2007.

Cowings, P.S., Suter, S., Toscano, W.B., Kamiya, J., Naifeh, K., "General Autonomic Components of motion sickness", NASA report, 1986.

Wiki How "How to Avoid Car Sickness" downloaded May 2013.

* cited by examiner

Figure 1 Mean heart rate at the baseline (Base) and at each rating of motion sickness (ratings as defined in Table 1).

SYSTEM AND METHOD FOR DETECTING MOTION SICKNESS

CROSS REFERENCE TO RELATED APPLICATIONS

This application is a U.S. national phase application of International Application No. PCT/EP2018/082141 filed on Nov. 22, 2018, which claims the benefit of EP Application Serial No. 17205374.6 filed on Dec. 5, 2017 and are incorporated herein by reference.

FIELD OF THE INVENTION

The invention relates to the detection of the onset of motion sickness using analysis of video images.

BACKGROUND OF THE INVENTION

It is possible to analyze video sequences of a living subject and detect small changes in the images which are the result of physiological processes of that subject. Amongst these physiological process are such things as blood flow, breathing and sweating. The measurement results of these processes are often referred to as vital signs.

Certain physiological processes can be observed via skin reflectance variations. The human skin can be modelled as an object with at least two layers, one of those being the epidermis (a thin surface layer) and the other the dermis (a thicker layer underneath the epidermis). A certain percentage 5% of an incoming ray of light is reflected at the skin surface. The remaining light is scattered and absorbed within the two skin layers in a phenomenon known as body reflectance (described in the Dichromatic Reflection Model). The melanin, typically present at the boundary of epidermis and dermis, behaves like an optical filter, mainly absorbing light. In the dermis, light is both scattered and absorbed. The absorption is dependent on the blood composition, so that the absorption is sensitive to blood flow variations. The dermis contains a dense network of blood vessels, about 10% of an adult's total vessel network. These vessels contract and expand according of the blood flow in the body. They consequently change the structures of the dermis, which influences the reflectance of the skin layers.

Other physiological processes such as breathing cause movement in the surface of patient.

Other physiological processes such as variations in blood oxygenation level can manifest themselves as small colour changes.

It is possible to detect and extract signals which have some periodic content in these changes and from that obtain a result such as a frequency in the case of periodic processes. For example, a subject may be illuminated with ambient light and filmed using a video camera. By analyzing changes in the values of corresponding pixels between frames of the sequence of images, a time-variant signal can be extracted. This signal may be transformed into frequency-like domain using something like a Fast Fourier Transform and from the frequency-domain spectra, a value for the subject's heart-rate may be arrived at as a physiological measurement. These physiological measurements are often called vital signs.

Motion sickness is experienced by many people, particularly when they are transported in some form of vehicle. Various theories to explain its occurrence, the most common of which postulates that a disagreement between visual and vestibular perceptions of movement sets up a condition of sensory conflict which then leads to the common symptoms such as nausea and dizziness. The effects can be rather debilitating for some people. A way of preventing motion sickness or reducing its severity would be beneficial. As in many afflictions, an early response or attempt to remedy is helpful. Therefore detection of its onset is useful.

SUMMARY OF THE INVENTION

Thus there is provided a method for reducing motion sickness in a subject which comprises detecting an onset of motions sickness which comprises receiving a sequence of video images, extracting measurements of a heart-rate of the subject over a plurality of time windows for first period of time from the sequence of video images using photoplethysmography (PPG), calculating at least one trend in the measurements, determining a presence of motion sickness when the at least one trend is positive over a first time window, the first time window being included in the first period of time, and generating an event arranged to generate a corrective action.

It is often possible to detect the onset of motion sickness before the subject actually feels the symptoms. Indeed, by the time the symptoms appear, corrective action is much less effective. Therefore, by detecting the onset early and alerting the subject so that they can react, it is possible to avoid the attack of motion sickness or, at least, reduce significantly its effects. By observing a positive trend in the heart-rate, a determination of the onset of motion sickness may be made before the subject is actually aware of the oncoming attack.

In an embodiment, the method further comprises determining the absence of a negative trend in the heart-rate as observed during the plurality of time windows subsequent to the first time window. In this way changes in heart-rate, which occur frequently and for many other reasons, can be excluded so as to avoid false alerts.

In an embodiment, the determining is repeated a plurality of times windows and successive positive determinations are interpreted as indicating an increase in motion sickness severity. This may be used in conjunction with a threshold so as to set the point at which an onset is determined. The use of a threshold opens the opportunity to set different thresholds for different subjects.

In an embodiment, the corrective action comprises providing to the subject suggestions including at least one of looking out of a window, getting fresh air, adapting driving style and performing breathing exercises. Such actions can have the benefit of preventing the onset or reducing its severity. Actually proposing actions improves the chances that the subject will react quickly enough for the remedies to be effective.

In an embodiment, the method further comprises providing guidance to the subject for the performing of the breathing exercises. Such exercises can have the effect of preventing the onset or reducing its severity. Proposing them to the subject can be useful in cases where the subject does not know how to do them.

In an embodiment, the corrective action comprises when used in conjunction with a virtual reality system, applying changes to at least one of the motion of objects displayed by the virtual reality system and the display frame rate of the virtual reality system. By reducing the speed of the changes in the visual stimuli, the difference between the visual information and that coming from the body's balance system which can help to prevent the attack or reduce its severity.

In an embodiment, the method may further comprise measuring the pallor of an area of facial skin of the subject by analysis the sequence of video images, the analysis comprising measuring changes in the intensity of a plurality of signals, each at different wavelengths, over a second period of time, determining a change over time of a ratio of the intensities, a certain change over time being indicative of an increase in pallor, wherein the determining of the onset includes determining an increase of pallor of the said area.

In an embodiment, the method may further comprise measuring changes in a respiration rate using analysis of the video sequence and wherein the determining of the onset includes determining the presence of respiratory sinus arrhythmia (RSA).

In an embodiment, the method may further comprise measuring a pattern of acceleration of the head of the subject using analysis of the video sequence, wherein the determining of the onset includes determining the presence of a repetitive acceleration with a frequency between 0.1 and 0.3 Hz.

In an embodiment, the method may further comprise the measurement of a pattern of motion of the subject using motion sensors, determining an onset of motion sickness according to a presence of a correlation in time between moments where RSA is present and the pattern of motion.

By combining hear-rate measurement with one or all of skin pallor, RSA, accelerations in the movements of the subject's head and correlations between the subject's motion and the presence of RSA, a quicker detection of an onset and/or a more reliable determination may be obtained.

In an aspect, there is also provided a system for reducing motion sickness in a subject in motion which comprises a processing unit configured to detect an onset of motion sickness, the processing unit comprising an input to receive a sequence of video images of at least one portion of a skin area of a subject, a physiological measurement unit configured to extract measurements of a heart-rate of the subject over a first period of time using from the sequence of video images using photoplethysmography (PPG), a calculation unit configured to calculate at least one trend in the measurements, a decision unit configured to determine a presence of motion sickness when the at least one trend is positive over a first time window, the first time window being included in the first period of time, and to generate a trigger event arranged to generate corrective action.

In an embodiment, the decision unit is further configured to determine the onset by determining the absence of a negative trend in the heart-rate is observed during a plurality of time windows subsequent to the first time window.

In an embodiment, the system may further comprise a coaching unit configured to provide the subject with suggestions for preventive action, the suggestions comprising at least one of looking out of a window, getting fresh air and performing breathing exercises.

In an embodiment, physiological measurement unit is configured to measure the pallor of an area of facial skin of the subject by measuring changes in intensities of a plurality of signals, each signal being at a different wavelength, over a second period of time, and to determine a change over time of a ratio of the intensities, the change over time of the ratio indicating an increase in pallor, wherein the determining of the onset includes determining an increase of pallor of the said area.

In an embodiment, the physiological measurement unit is further configured to measure changes in a respiration rate and wherein the determining of the onset includes determining the presence of respiratory sinus arrhythmia (RSA).

In an embodiment, the processing unit may further be configured to measure a pattern of acceleration of the head of the subject using analysis of the video sequence, wherein the detection of the onset includes determining the presence of a repetitive acceleration with a frequency between 0.1 and 0.3 Hz.

There is also provided a computer software product which, when run a computer processing system, causes the computer processing system to execute any of the above mentioned aspects and embodiments.

BRIEF DESCRIPTION OF THE DRAWINGS

The above, as well as additional objects, features and advantages of the disclosed devices, systems and methods, will be better understood through the following illustrative and non-limiting detailed description of embodiments of devices and methods, with reference to the appended drawings, in which.

DETAILED DESCRIPTION OF THE EMBODIMENTS

In the following description, same references designate like elements.

Figure 1:
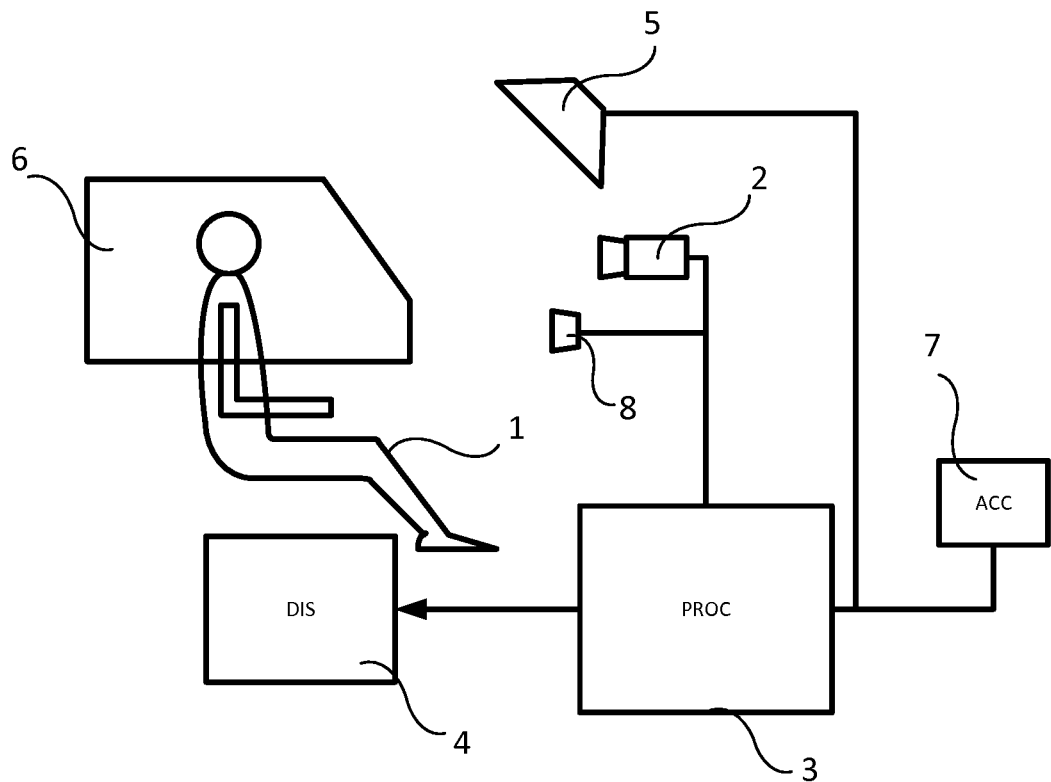
FIG. 1 represents a system according to an embodiment in an exemplary use case.

FIG. 1 represents situation where an embodiment is employed. A person or subject 1 is sat in a seat of a vehicle in motion (not shown). A camera 2 is arranged to have a frontal view of the person 1, preferably including the person's head and thorax. The camera 2 is coupled to a processing unit 3 (PROC) and the camera 2 feeds a sequence of video images to the processing unit 3. The signal processing unit 3 is further coupled to a display 4 (DIS) and an optional illumination source 5 so that the processing unit 3 may control the illumination source 5 (where present). The person 1 is optionally flanked by a window 6 and preferably the window 6 may be opened so as to increase the flow of air from outside into the vehicle. Optionally there is a motion sensor 7 (ACC) coupled to the processing unit 3. The motion sensor 7 may be implemented by an accelerometer, a gyroscope or some combination thereof and ideally, will be sensitive to movements in the range of 0.1 to 0.3 Hz which is the range that many people are sensitive to. It would also be good to include the typical frequency range of the intended vehicles. For cars, movements may have frequencies around 1 Hz whereas for boats or ships it may be much lower, for example in the hundredths of Hz. Optionally there is one or more IR sensors 8, arranged to measure the skin temperature of the person 1. The IR sensor (or sensors) 8 would ideally be positioned to as to observe skin areas of the person 1. The IR sensor(s) 8 could be arranged in the camera 2 but it is possible the greater accuracy could be achieved by having them separate. The illumination source 5 may be configured to illuminate the person with light of the frequency range being used for the PPG.

Though other methods could be used for measuring the vital sign in question (for example contact sensors for heart rate), a camera-based method has an advantage in that it is non-invasive (in the sense that the people do not need to connect themselves or be touched by something) and one equipment can monitor multiple people.

Figure 2:
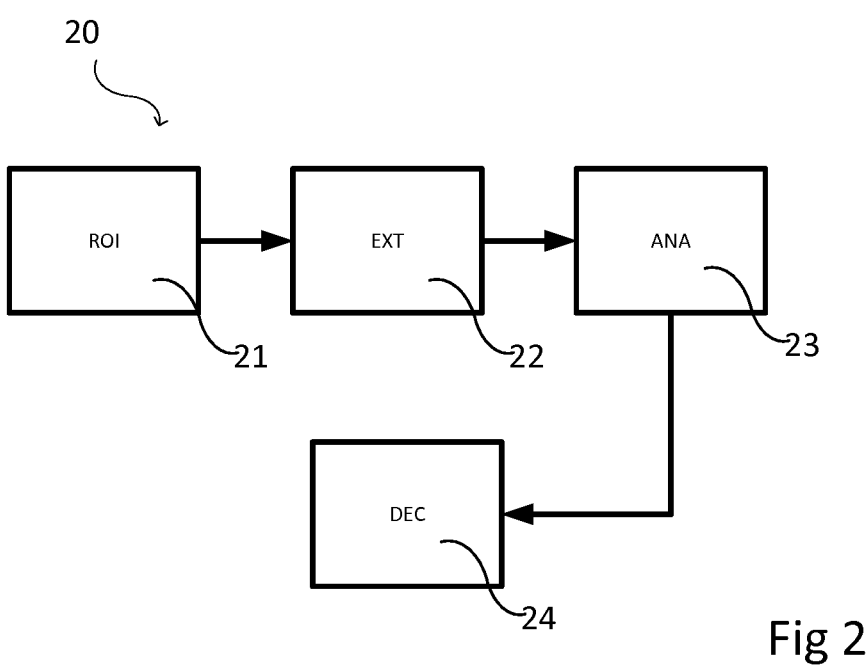
FIG. 2 represents component parts of a system according to an embodiment.

FIG. 2 represents the processing chain 20 which is implemented in the processing unit 3. Some areas, such as those containing exposed skin, and in particular that of the face and neck, often contain a stronger signal. Areas covered by clothing are often poor choices for signal extraction. Therefore, it is desirable to select certain parts of each frame of the video sequence for analysis. Since the signal is derived from changes between frames of the video sequence, the selected regions can be considered as making up series or groups and it is desirable that selected regions of a group all correspond as well as possible to the same actual region of the person. A patch selecting unit 21 (ROI) selects the patches or ROIs that are to be tracked. There may be one or more patches which are selected for subsequent processing. There will be most probably a significant level of relative movement between the person 1 and the camera 2 and so it is desirable to compensate for this motion as best as possible. The patch selecting unit 21 performs the motion compensation on the images with reference to the selected patches in order to feed a series of motion compensated patches to a signal extractor 22 (EXT). One method of motion compensation uses two adaptive filters which filter the (mean) x- and y-motion of the skin region of interest, provided as input x-y-motion signals which are derived from the analysis of the individual images. It should be noted that the number of two filters and the use of two motion signals (for motion in x-direction and y-direction) are not mandatory. Generally, one filter and one motion signal in a desired direction (e.g. of assumed strongest motion) or more filters and more motion signals (in desired directions) can also be used. The coefficients of the adaptive filters may be updated by means of a normalized least-mean-square (NLMS), but other adaptive algorithms can be used. The signal extractor 22 performs operations on the signal in order to arrive at the time-varying signal of interest. These operations may include the combining of the colour channels and/or the normalizing of the signal. It may be that the sequence of patches has been broken up into shorter sequences in order to make the task of motion compensation easier. In this case, the extraction unit 22 may also combine the shorter sequences into longer sequences. The extracted time varying signal is then fed to a signal analyzer 23 (ANA) which, in a role of a physiological information calculator, performs operations in order to arrive at the physiological information or vital sign result of interest.

The patch selecting unit 21, the signal extracting unit 22 and the signal analyzer 23 may be implemented in a one or more general purpose processors running appropriate software. This has the advantage of being possible with pre-existing hardware and allows for subsequent modification and tuning. However it can result in a solution which is slower and/or more expensive than a mode dedicated solution. Alternatively they may be implemented in microcontrollers running firmware designed to implement the relevant functions. This solution may be less expensive when production volumes are sufficiently high enough. Yet another possibility is to implement the functions in dedicated hardware. In high volumes, this is often cheaper and gives higher processing speed per unit cost.

The patch selecting unit 21 selects the patches using one or more of a number of methods. A process which is sometimes called 'segmentation' is performed. It is convenient to start by selecting the general area of interest. The face is suitable whenever blood flow is the physiological process of interest so a face-identification algorithm may be used. A suitable algorithm for implementing face detection is described in Viola, P. and Jones, M. J., "Robust real-time object detection", *Proc. of IEEE workshop on statistical and computational theories of vision,* 13 Jul. 2001. Alternative algorithms for recognizing shape and colour patterns also exist and these may be used for detecting the facial area. For other processes like breathing, other methods for identifying the thorax may be used.

Also the blocks may be classified as being skin areas or not by comparing the relative values of the colours in each pixel therein and absolute intensities of those pixels. Analysis of colour gradients inside and between blocks can also be helpful for identifying skin areas. Identifying skin areas is made more difficult by the wide variety of possible skin tones and account should be taken of this.

A decision unit 24 (DEC) analyses certain characteristics, such as trends over time, of the physiological information result in order to detect the presence of, or preferably an onset of, motion sickness in the person 1.

It turns out that there is a correlation between changes in a person's vital signs and motion sickness that they are experiencing.

Figure 3:
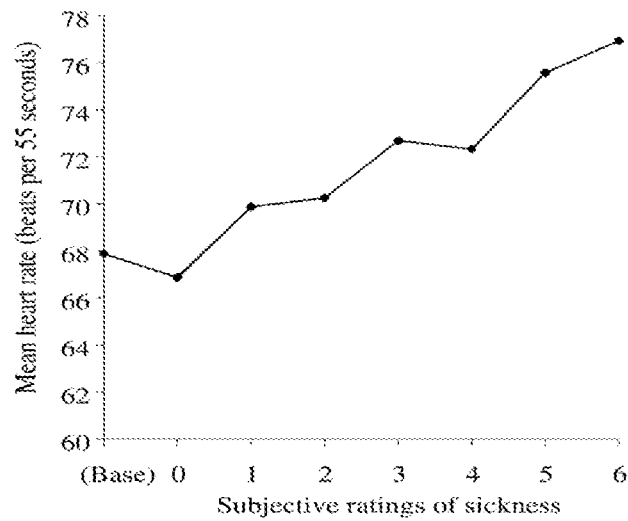
FIG. 3 represents a curve of heart-rate vs perceived level of motion sickness.

FIG. 3 shows a graph of mean heart rate as a function of perceived severity of motion sickness from 'Holmes, S. R. and Griffin, M. J., "Correlation between heart rate and the severity of motion sickness caused by optokinetic stimulation", *Journal of Psychophysiology,* 15, pg. 35-42, 2001'. From this it can be seen that there is a positive correlation between increases in heart rate and the presence of motion sickness.

Respiratory sinus arrythmia is a phenomenon observed in many vertebrates including man. It is a variability in the R-R interval which is effectively the inverse of the heart rate which is synchronised with respiration in that the heart rate increases during inspiration and decreases during expiration. It appears that the degree to which this happens decreases in a person when they are experiencing motion sickness. The article 'Gianaros, P. J., Quigles, K. S., Muth, E. R., Levine, M. E., Vasco Jr, R. C., Stern, R. M., "Relationship between temporal changes in cardiac parasympathetic activity and motion sickness severity", Psychophysiology, 40(1): 39-44, 2003', reports the following table:

Average Motion Sickness Score, RSA, and Respiratory Rate by Time Period

| Measure | Time period | | | |
|---|---|---|---|---|
| | Baseline | Rotation min 4 | Rotation min 7 | Rotation min 10 |
| PDI | 1.28 (0.20) | 4.64 (0.44) | 6.10 (0.58) | 7.16 (0.60) |
| RSA | 6.64 (0.11) | 6.45 (0.14) | 6.23 (0.16) | 6.28 (0.13) |

Average Motion Sickness Score, RSA, and Respiratory Rate by Time Period

| | Time period | | | |
|---|---|---|---|---|
| Measure | Baseline | Rotation min 4 | Rotation min 7 | Rotation min 10 |
| Corrected RSA | .25 (.05) | .12 (.04) | −.10 (.05) | −.06 (.04) |
| Resp. rate | 15.72 (0.43) | 16.14 (0.49) | 15.56 (0.47) | 15.01 (0.42) |

Note.
PDI: Pensacola Diagnostic Index (arbitrary units); RSA: Respiratory sinus arrhythmia (in units); Corrected RSA: Respiratory-rate-adjusted RSA values; Resp. Rate5Respiration rate (breaths per minute). Values in parentheses indicate standard error of the mean.

where it can be seen that the most significant observable change is in the first 4 minutes or so.

RSA can be quantified in a number of different ways, most commonly including spectral analysis, time-domain peak valley analysis or application of a band-pass filter. Units of measurement can also consequently vary. For time-domain measures, RSA is typically estimated in ms (e.g. the inspiratory-expiratory difference in RRI). With spectral analysis and other frequency-domain approaches, the variation of RRI occurring within the range of the respiratory frequency is estimated; thus ms2 is frequently employed, consistent with usual statistical units of variance. Often RSA measures are logarithmically transformed to normalize distribution, but this is not always the case. However, the important thing to note is that the largest change is noted in the first four minutes so the exact physical significance of the quantities is not important but the change is. The skilled person may choose the units to suit the convenvience of the details of the implementation of the calculations.

Therefore measurements and detection of trends in these vital signs or physiological parameters may be used to detect the presence or onset of motion sickness and observe its progression.

Figure 4:
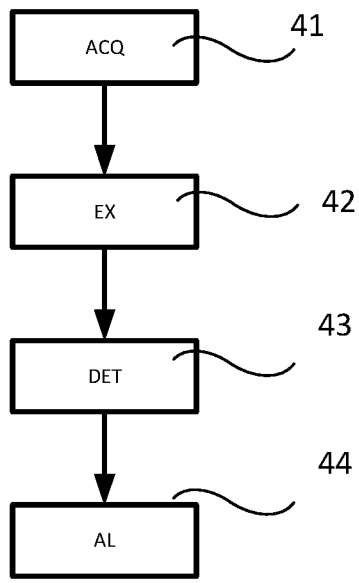
FIG. 4 represents a summary of a flow according to an embodiment.

FIG. 4 represents a high level flow for the measurement of a vital sign or physiological information according to an embodiment and the subs. At step 41 (ACQ) a sequence of video images is acquired. At step 42 (EX), the sequence of video images is then analysed and a signal representing the vital sign or physiological information is extracted in the manner described with reference to FIG. 2. At step 43 (DET), the signal is analysed for characteristics indicative of motion sickness and at step 44 (AL), if a positive determination for motion sickness is made, an trigger event is generated.

Figure 5:
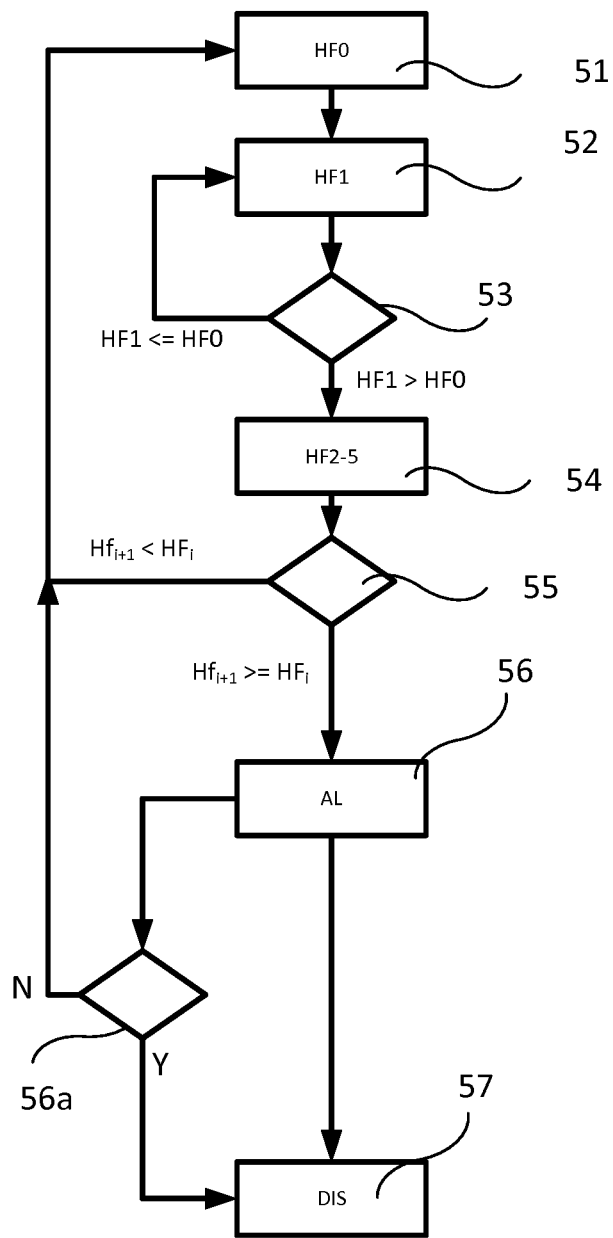
FIG. 5 represents a detailed part of a flow according to an embodiment.

FIG. 5 represents a decision process according to an embodiment for determining an onset or presence of motion sickness. The method involves a series of heart-rate measurements, made at regular intervals. At 51(HF0) a first heart-rate is measured over interval 0 and stored. At an interval later, at 52 a second measurement is made. At 53 the measurements are compared. If the second heart-rate measurement is not greater than the first, the first measurement is deleted and replaced by the second reading. Flow passes back to 52 where another measurement is made and then again to 53 where the two measurements are compared. If, however, the second measurement is greater than the first, the flow passes to 54 where 4 more measurements are made, again at the interval, and stored. At 55, these measurements are compared with their immediate predecessor (that is to calculating $HR_i - HR_{i-1}$). If none of the comparisons are negative (i.e. $HR_i < HR_{i-1}$), then the heart rate changes are judged significant and a positive determination of the presence or onset of motion sickness is made and, at 56 (AL), an alert status or flag (HeartRate) is set to be 'true', e.g. HeartRate=1, and at 57 a trigger event is generated. It should be noted that the steps 54 and 55 maybe combined such that each of HR3 to 6 is immediately compared to its predecessor rather than when all 4 have been measured. This way the return to 51 in the event of a negative change could be made earlier. It is also possible to make the whole series of measurements and then perform the successive difference calculations in one go. In this case the decision points 53/55 become a case of deciding whether or not to perform the subsequent difference calculations. The first method saves storing the full series and the second may save on computing complexity when very simple processing has been chosen.

Thus there is provided a method for reducing motion sickness in a subject which comprises acquiring a sequence of video images, extracting measurements of a heart-rate of the subject over a first period of time from the sequence of video images using photoplethysmography (PPG), calculating at least one trend in the measurements, determining a presence of motion sickness when the at least one trend is positive over a first time window, the first time window being included in the first period of time, and generating an event arranged to generate a corrective action.

It is often possible to detect the onset of motion sickness before the subject actually feels the symptoms. Indeed, by the time the symptoms appear, corrective action is much less effective. Therefore, by detecting the onset early and alerting the subject so that they can react, it is possible to avoid the attack of motion sickness or, at least, reduce significantly its effects. By observing a positive trend in the heart-rate, a determination of the onset of motion sickness may be made before the subject is actually aware of the oncoming attack.

Thus the decision unit 24 is configured to determine a presence of motion sickness when the at least one trend is positive over a first time window, the first time window being included in the first period of time, and to generate an trigger event arranged to generate corrective action. Also the decision unit may further be configured to determine the onset by determining the absence of a negative trend in the heart-rate observed during a plurality of time windows subsequent to the first time window.

Heart-rate can vary quickly and in an apparently erratic manner for unrelated reasons and for the purposes of this method, these variations can be considered as noise. Therefore, it is better to make each measurement over a short period of time and take an average value from that period. The longer each period is, the better the averaging can remove the noise but this is multiplied by 6 making the overall process longer, thereby delaying the trigger event. Also, it may be desirable to monitor the person 1 continuously and in this case, a longer process would result in less frequent decision points. Since it is preferable to take action as early as possible, it is desirable that the process not take too long. This is because it is much easier to prevent a full attack in the early stages—once the nausea has become noticeable, it is often too late. A convenient period is around a minute for each measurement i.e. the above sequence would consist of 6 1-minute periods. A minute, or thereabouts, for each allows the averaging to remove random variations whilst not making the overall routine too long to execute. However other period lengths remain possible and the sequence length may be made shorter or longer. Also a number of periods other than 6 may be used.

In an embodiment, the alert flag is extended to being an alert level, for example a counter. In this case at 56, the alert level is increased, for example by incrementing the counter. In this embodiment, flow passes to 56a where the alert level is compared to a threshold. Where the alert level equals or exceeds the threshold, flow passes to 57, otherwise the flow returns to 51 for another 6 measurement periods. In a further variant of this embodiment, rather than the flow passing back to 51 for another execution of 6 measurement periods, each period is compared with its predecessor, $HF_7$-$HF_6$ and so on. At each positive result of ($HR_i$-$HR_{i-1}$), the alert level is increased. The difference between this last variant and where the alert level increments are only made once every 6 measurement periods is that the threshold may be reached more quickly, resulting in an earlier trigger event.

The trigger event can also cause the providing of suggested courses of action for the person 1. Many sufferers of motion sickness say that looking outside, for example toward the horizon helps. However this is not known by everyone so suggestions could be made for the person to look outside the window. Breathing fresh air has also be found be certain sufferes to help. Therefore this could be proposed. Breathing exercises have shown positive effects for certain people where rhythmic motion of the vehicle is present. It seems that matching exhalation to backward tilts or attempting to avoid the breathing rate becoming synchronised with the motion can be helpful. In the case where the motion sensor 7 is present, the measured motion frequency can be used to adapt the instructions, for example to slow down or speed up the breathing rate. It has also been observed that maintaining slow deep breathing can be helpful. Suggestions or even a short training or guidance in line with these possibilities could be displayed explaining this. Providing positive instructions may increase the chance that the subject actually reacts.

Furthermore, an estimation of the motion frequency can be obtained by analysing the motion of the head with respect to that of the torso. The determination of the motion frequency may also be achieved by using outward-facing camera, though this requires more equipment.

Thus system may further comprise a coaching unit configured to provide the subject with suggestions for preventive action, the suggestions comprising at least one of looking out of a window, getting fresh air and performing breathing exercises.

Monitoring of the person 1 may continue in order to provide a feedback system. For example, if it is noticed that the heart-rate still remains above the initial value in the sequence of measurements from which the trigger event was generated, this could be indicated in the suggestions or, where breathing exercise training is being employed, adapt the instructions. Or, where a drop in heart-rate is seen, the instructions can adapted accordingly—for example letting the subject know they can stop the exercises or close the window more.

In an autonomous vehicle, the trigger event could also be used to adapt the driving style of the vehicle, for example, driving more slowly and make direction changes more gentle. Or where the subject in question is not the driver, suggestions could be made to the driver to adapt their driving style.

In an embodiment, a measurement of changes in overall skin pallor are made. It has also been observed that some sufferers become paler during an attack of motion sickness. Since the tint of peoples' skin varies somewhat, it is the change of colour toward a paler tint that is looked for. The increase in pallor is due to a reduction in the amount of oxyhaemoglobin in the outer skin layers which consequently changes the absorption spectrum of the skin. For a single location of the skin, the light absorption property at two distinct wavelengths of the reflected light spectrum may be measured by the system, and the ratio of both absorption properties is calculated. Assuming that the light spectrum of the incident light remains unchanged, a change in the calculated ratio is a result of a change in density of a skin tissue. The sensitivity to hemoglobin concentrations or densities can be obtained by choosing the two wavelengths which, on one hand, show a large difference in the absorption levels for hemoglobin between them, but where the difference between them is small for the absorption spectrum of all other skin tissue components on the other hand. Where infrared is being measured (for example by having at least some pixels of the sensor without the infrared filter), the wavelengths could for instance be just below 700 nm (where there is a dip in curve of the absorption spectrum for oxyhemoglobin) and for 900 nm (where there is a peak in the curve of the hemoglobin absorption spectrum). More than two wavelengths may be used. By observing changes in the ratio of the intensities of reflected radiation at these two (or more) values and determining that the level of oxyhaemoglobin levels in the skin have dropped, an increase in skin pallor may be deduced. Where it is observed that the skin is becoming paler, this can be taken as an indication of an onset of motion sickness.

In an embodiment, compound ratios may be used. For example, a first ratio between the reflected light at each of two wavelengths could be calculated from readings taken at a first time. Then a second ration could be calculated between the reflected light at the two wavelengths measured at a second time. A ratio between the two ratios could be calculated. This can make the measurements less sensitive to changes in hemoglobin concentrations/densities brought about by other physiological changes. The method of measurement of skin pallor changes may be used in conjunction with the measurement of heart-rate changes described previously when the camera is adapted to receive in both the visible part of the spectrum and the two wavelengths mentioned above. Many modern cameras have CMOS image sensors which, when destined for use in visible wavelengths have an infrared filter. By arranging for a portion of the pixels to not have the infrared filter, the wavelengths around the 700 and 900 nm could be detected whilst the other pixels could be used in the visible part of the spectrum for the PPG.

There is a number of ways of implementing a decision process using both skin pallor and heart-rate. For example, in a simple version, the flag set under control of the heart-rate could be complemented by a flag set under the control of the skin pallor (SkinPallor=1) in that the trigger event is generated when both are true. This could improve the overall reliability of the determination which, in turn, will encourage the subject to have confidence in the system and react—any history of overly frequent or false alerts will damage confidence and reduce the likelihood that subject reacts. Alternatively, a positive result from the skin pallor method could cause an increase in the alert level. Since the detection of a skin pallor change may be possible earlier than the 6 periods for the heart-rate measurement, another embodiment uses the skin pallor flag to change the flow of the heart-rate measurement. Rather than having the measurements from periods 2 to 6 act simply as confirmations after a positive difference between two successive measurements has been obtained (a 'yes' at the decision point 53), whenever SkinPallor=1, each positive result of $(HR_i\text{-}HR_{i-1})$ causes an increase in the alert level. In this embodiment, the alert level may reach the threshold faster.

It is also possible to measure movements of the person's 1 head from the sequence of video images and this is used in an embodiment. As explained earlier, motion compensation is typically used in tracking the patches from which the vital sign signal is to be extracted. Usually this motion compensation involves calculating motion vectors which characterise the motion of patch being tracked. Where the selected patches are on the person's 1 head, these motion vectors can be analysed to deduce the actual motion of the head and, if the video sequence is captured over a long enough time (the length of time for the sequence described in relation to FIG. 5 should be enough), repetitive accelerations of the head can be detected and their frequency obtained. The skilled person will be able to choose the exact method of this analysis. As stated before, people are typically sensitive to frequencies in the range of 0.1 to 0.3 Hz. If motion of the person's 1 head is detected in this significant range, a head motion flag may be set (for example, HeadMotion=1). This holds for motion in both horizontal and vertical directions. This head motion flag may be used in a similar way to the skin pallor flag. Where both skin pallor and head motion are measured, an combination of the two flags may be used in the place of the individual ones and that used with the heart-rate measurements, as described previously. Where the motion sensor 7 is being used, the detection of significant motion in the frequency ranges of interest can be used to set a flag (for example, VehicleMotion=1). This vehicle motion flag can be used in the same way as the skin pallor and head motion flags i.e. on its own or combined with other flags being used. Ways of using the flags in a combined way include using a truth-functional operator which evaluates an inclusive disjunction (for example OR'ing).

The threshold level may be a standard preset value or may be adapted over time to the person 1. A standard preset value, for example alert level above 2 or 3 being enough to determine an onset, is simpler and so cheaper to implement but may produce either false positives or generate trigger events too late. One way of adapting the threshold to the person is to classify the person into one of three broad categories, high, medium and low susceptibility. This classification could be, for example, be achieved by asking the person. Then the thresholds can be set accordingly. Alternatively, the increment by which the alert level increases per increase in heart-rate could be increased for higher susceptibilities. This takes advantage of the fact that the higher the susceptibility, the earlier, in general, will the signs of onset be seen. A further alternative could be to generate the trigger event after fewer periods, as in the example concerning the use of heart-rate changes in conjunction with skin pallor.

Another way of adapting the alert threshold value to the person can be accomplished either by having the person 1 enter an identification or by using face recognition to store an identity for the person 1. Then an individual threshold can be associated with that identity and the results obtained over longer periods i.e. longer than the measurement cycles described above for that person may be stored and/or used in calculations to calculations to adapt the threshold. In a particular version of this embodiment, whenever an trigger event is generated, the system can request a confirmation from the person 1 that they felt some symptoms of motion sickness. If they respond with a yes, the threshold can be lowered because the system is not generating the trigger event early enough and if they respond with a no, it can be raised until the responses have shown oscillation between yes and no, indicating that the threshold is adapted to that person. Avoiding false positives may help avoid nuisance to the person, for example having them open a window in cold weather. Avoiding late trigger events is desirable for the reasons mentioned previously. Other personlisations could be to request the person enter data such as gender, age. The latter may also be estimated using the images in order to select between broad classifications such as baby (0-2), child (3-12), teenager (12-18), adult (18 and up). In such a system, a preset threshold would be needed when the system is used for the first time.

Another approach to combining the various indications (heart-rate increases judged significant by the routines described above, presence of RSA, changes in skin pallor, presence and degree of motion in a significant frequency range and skin temperature) could be by adding weighted results. The adapting of the weightings and thresholds may be achieved using machine-learning techniques such as neural networks and mathematical techniques such as hidden or semi-hidden Markov models. The learning process could be to identify correlations between indications and correlations between the indications and responses from the person 1 concerning their experience of motion sickness. In such a case, the initial settings could be set with default values. The default values could be weighting higher the heart-rate, for example that of the other indications which would all start with the same weighting. Alternatively, where population statistics have become available, the weightings and threshold could be set according to these.

Examples concerning use in vehicles and persons in motion have been discussed. Another are where motion sickness occurs is in the use of computer simulated environments such as virtual reality, such as in games, and similar principles apply. Some people experience motion sickness for similar reasons to those arising for passengers. In the case of simulations or virtual reality, the system and method could be used to detect the onset and then either advise the person and/or adapt the display, for example by reducing the speed and/or amplitude of the movement of objects in the display or by slowing the frame-rate so as slow down changes in what is displayed. A feedback system could be used whereby continuous monitoring could be used to effect gradual changes in the display so as to limit the disturbance to the person. Other situations could be in the use of equipment like flight simulators.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer or processing unit. In the device claim enumerating several means, several of these means may be embodied by one and the same item of hardware. The mere fact that certain measures are recited in mutually different dependent claims does not indicate that a combination of these measures cannot be used to advantage.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

Storage media suitable for storing computer program instructions include all forms of nonvolatile memory, including but not limited to EPROM, EEPROM and flash memory devices, magnetic disks such as the internal and external hard disk drives, removable disks and CD-ROM disks. The computer program product may be distributed on such a storage medium, or may be offered for download through HTTP, FTP, email or through a server connected to a network such as the Internet.

The invention claimed is:

1. A method for reducing motion sickness in a subject, the method comprising:
    detecting an onset of the motion sickness, wherein the detecting of the onset of the motion sickness comprises:
        receiving a sequence of video images,
        extracting measurements of a heart-rate of the subject over a plurality of time windows for a first period of time which comprises the plurality of time windows, wherein the measurements are extracted from the sequence of video images using photoplethysmography (PPG),
        calculating at least one trend in the measurements, and
        determining a presence of motion sickness when the at least one trend is positive over one of the plurality of time windows, and there is no negative trend observed over any of the time windows of the first period of time; and
    generating an event arranged to generate a corrective action.

2. The method of claim 1, wherein successive positive determinations over the plurality of time windows are interpreted as indicating an increase in motion sickness severity.

3. The method of claim 1, wherein the corrective action comprises providing to the subject suggestions including at least one of: looking out of a window, getting fresh air, adapting driving style and performing breathing exercises.

4. The method of claim 3, further comprising providing guidance to the subject for the performing of the breathing exercises.

5. The method of claim 1, wherein the corrective action comprises. when used in conjunction with a virtual reality system, applying changes to at least one of: a motion of objects displayed by the virtual reality system, and a display frame rate of the virtual reality system.

6. The method of claim 1, further comprising:
    measurement of pallor of an area of facial skin of the subject by analysis of the sequence of video images, the analysis comprising measuring changes in an intensity of a plurality of signals, each at different wavelengths, over a second period of time; and
    determining a change over time of a ratio of the intensities, wherein a certain change over time is indicative of an increase in pallor,
    wherein the determining of the onset includes determining an increase of the pallor of the area.

7. The method of claim 1, further comprising measuring changes in a respiration rate using analysis of the video sequence and wherein the determining of the onset includes determining the presence of respiratory sinus arrhythmia (RSA), wherein determining the presence of RSA comprises detecting a synchronization between an R-R interval and a respiration of the subject.

8. The method of claim 1, further comprising measuring a pattern of acceleration of the head of the subject using analysis of the video sequence, wherein the determining of the onset includes determining the presence of a repetitive acceleration with a frequency between 0.1 and 0.3 Hz.

9. The method of claim 8, further comprising:
    measuring a pattern of motion of the subject using motion sensors; and
    determining an onset of motion sickness according to a presence of a correlation in time between moments where respiratory sinus arrythmia (RSA) is present and the pattern of motion.

10. A system for reducing motion sickness in a subject in motion, the system comprising:
    a processing unit configured to detect an onset of the motion sickness, wherein the processing unit comprises:
        an input to receive a sequence of video images of at least one portion of a skin area of a subject,
        a physiological measurement unit configured to extract measurements of a heart-rate of the subject over a plurality of time windows for a first period of time which comprises the plurality of time windows, wherein the measurements are extracted from the sequence of video images using photoplethysmography (PPG), and
        a calculation unit configured to calculate at least one trend in the measurements; and
    a decision unit configured to determine a presence of motion sickness when the at least one trend is positive over at least one of the plurality of time windows and there is no negative trend observed over any of the time windows of the first period of time, and to generate a trigger event arranged to generate corrective action.

11. The system of claim 10, further comprising a coaching unit configured to provide the subject with suggestions for preventive action, the suggestions comprising at least one of: looking out of a window, getting fresh air and performing breathing exercises.

12. The system of claim 10, wherein the physiological measurement unit is configured:
    to measure a pallor of an area of facial skin of the subject by measuring changes in intensities of a plurality of signals, each signal being at a different wavelength, over a second period of time, and
    to determine a change over time of a ratio of the intensities, the change over time of the ratio indicating an increase in the pallor, wherein the determining of the onset includes determining an increase of the pallor of the area.

13. The system of claim 10, wherein the physiological measurement unit is further configured to measure changes in a respiration rate and wherein the determining of the onset includes determining the presence of respiratory sinus arrhythmia (RSA).

14. The system of claim 10, wherein the physiological measurement unit is further configured to measure a pattern of acceleration of the head of the subject using analysis of the video sequence, wherein the determining of the onset includes determining the presence of a repetitive acceleration with a frequency between 0.1 and 0.3 Hz.

15. A computer software product which, when run a computer processing system, causes the computer processing system to execute the method of claim 1.

16. The system of claim 10, wherein successive positive determinations over the plurality of time windows are interpreted as indicating an increase in motion sickness severity.

17. The system of claim 11, further comprising providing guidance to the subject for the performing of the breathing exercises.

18. The system of claim 10, wherein when used in conjunction with a virtual reality system, the corrective action comprises applying changes to at least one of: a motion of objects displayed by the virtual reality system, and a display frame rate of the virtual reality system.

19. The system of claim 14, wherein the physiological measurement unit is further configured to:

measure a pattern of motion of the subject using motion sensors; and determine an onset of motion sickness according to a presence of a correlation in time between moments where respiratory sinus arrhythmia (RSA) is present and the pattern of motion.

20. The method of claim 1, wherein determining the presence of motion sickness when the at least one trend is positive over one of the plurality of time windows, and there is no negative trend observed over any of the time windows of the first period of time, comprises:

determining the heart-rate in each of the time windows of the first period of time;

comparing the heart-rate in each time window of the first period of time with the heart-rate in an immediately-succeeding time window of the first period of time; and determining a presence of motion sickness when the heart-rate increases from at least one of the time windows to the immediately-succeeding time window of the first period of time, and never decreases from any of the time windows to the immediately-succeeding time window of the first period of time.

* * * * *